(12) United States Patent
Eckert et al.

(10) Patent No.: US 8,295,903 B2
(45) Date of Patent: Oct. 23, 2012

(54) ELECTRON AVALANCHE PUTATIVE ENERGY FIELD ANALYZER

(75) Inventors: Bryon K. Eckert, Lanham, MD (US); Bradley N. Eckert, Mesa, AZ (US)

(73) Assignee: Auraprobe, Inc., Mesa, AZ (US)

( * ) Notice: Subject to any disclaimer, the term of this patent is extended or adjusted under 35 U.S.C. 154(b) by 810 days.

(21) Appl. No.: 12/472,174

(22) Filed: May 26, 2009

(65) Prior Publication Data

US 2009/0292196 A1    Nov. 26, 2009

Related U.S. Application Data

(60) Provisional application No. 61/056,000, filed on May 25, 2008.

(51) Int. Cl.
 *A61B 5/00* (2006.01)
(52) U.S. Cl. ........................................................ 600/407
(58) Field of Classification Search ................... 600/300, 600/407
 See application file for complete search history.

(56) References Cited

U.S. PATENT DOCUMENTS

| | | | |
|---|---|---|---|
| 4,328,809 A | 5/1982 | Hirschowitz et al. | |
| 4,602,639 A | 7/1986 | Hoogendoorn et al. | |
| 4,834,111 A * | 5/1989 | Khanna et al. | 600/587 |
| 5,166,819 A * | 11/1992 | Eichel | 398/202 |
| 5,417,211 A | 5/1995 | Abraham-Fuchs et al. | |
| 5,646,526 A | 7/1997 | Takeda et al. | |
| 6,347,238 B1 | 2/2002 | Levengood et al. | |
| 6,466,688 B1 | 10/2002 | Ramstack | |
| 6,746,397 B2 | 6/2004 | Lee et al. | |
| 2004/0005124 A1* | 1/2004 | Gallup et al. | 385/88 |
| 2005/0018137 A1* | 1/2005 | Barth et al. | 351/221 |
| 2009/0140153 A1* | 6/2009 | Flamanc et al. | 250/368 |

* cited by examiner

*Primary Examiner* — Jonathan Cwern
(74) *Attorney, Agent, or Firm* — Etherton Law Group, LLC; Benjamin D. Tietgen; Sandra L. Etherton

(57) ABSTRACT

A device and method of detecting and analyzing a vital field places an avalanche diode in the path of vital waves in the vital field. The vital waves interfere with the electron avalanche process in the avalanche diode. Control circuitry and an avalanche initiator cause electron avalanches at a known sampling frequency. The interference from the vital waves produces a beat frequency that is output from the avalanche diode. By adjusting the sampling rate by a known amount, a second beat frequency is produced and the beat frequency shift is used to determine the input frequency of the vital waves. The vital waves are very weak and produce frequencies into the terahertz range, so that the input frequency is undersampled by the device. Further, high sensitivity is required and a circuit design is implemented to maximize sensitivity while minimizing noise and other interference that is common to avalanche diode operation.

10 Claims, 3 Drawing Sheets

ELECTRON AVALANCHE PUTATIVE ENERGY FIELD ANALYZER

CROSS-REFERENCE TO RELATED APPLICATIONS

This application claims the benefit of provisional application No. 61/056,000 filed May 25, 2008.

FIELD OF INVENTION

This invention relates to pattern analysis. This invention relates particularly to methods and devices for detecting and analyzing energy fields emitted by organisms.

BACKGROUND

All live organisms emit energy fields, referred to herein as vital fields, which are characterized by the organic processes that produce or modify them. There is a significant amount of skepticism surrounding vital fields because no known scientific instruments can detect them. The inability to detect, measure, and describe the energy in a vital field is a problem that inhibits human understanding of biological interactions with the environment.

A wave in an energy field is considered to comprise four components—electric, magnetic, gravitational and temporal. The electric, magnetic, and gravitational components are orthogonal to each other. In an electromagnetic wave, the gravitational and temporal components have a static value, and the electric and magnetic components vary inversely. In this context, a static temporal component equates to time moving forward at a constant rate. In contrast, a vital wave is theorized to contain static electric and magnetic components and dynamic temporal and gravitational components. Such a wave is essentially a longitudinal or compression wave in the space-time fabric. Because vital waves do not have a dynamic magnetic component, they do not induce a current in a conductor. Most known devices rely on such induction and is therefore unable to reliably detect the presence of vital waves or measure or describe them scientifically.

Kirlian photography, discovered in the early 20th century, can be considered one of the earliest means of analyzing vital fields. Kirlian photography works by driving a photographic plate at high voltage, with a biological specimen resting on the plate. The resulting image left on the film is consistent with the corona discharge pattern of the specimen. Live specimens tend to show a shimmering coronal effect, whereas dead specimens and inanimate objects exhibit a more uniform pattern. The difference is attributed to the live specimen having at least one vital field. It should be noted, however, that Kirlian photography as an indication of vital fields has been met with skepticism, with the results explained away as errors in the experimental process.

Most vital field detection devices to date have been either a variation of Kirlian high-voltage equipment or low voltage electric field sensors. One device, used to detect pathogens in an organism, places the organism in an electrical field and detects an aura signature of pathogens energized by the field. Another device uses a passive detector that characterizes pulses of charge transfer called charge density pulses through conductive plates placed near the palms of the hands. The decay envelope of the detected pulse train may provide information useful for analysis of the body's chakra regions. However, the data is extracted from a pulse train that does not achieve a steady state, and so the data that can be obtained is limited. Further, the data describing the electric component of present waves would not completely describe the temporo-gravitational wave because its electric component is static.

Some detectors, such as electrocardiographs and electro-encephalographs, analyze alternating current waveforms detected by electrodes placed on the skin of the test subject. One known device uses contacts on the palms and fingers to detect the physiological signals of the human body supposedly associated with auras. Other detectors introduce an electric current into the electrodes, such as with a galvanic skin response and others, which measure the organism's interaction with the introduced current through physical contact between the organism and the detector. Still other devices use capacitance to measure the interaction, but must be placed extremely close to the organism to be effective. Contact and capacitance based devices suffer significant problems with artifacts caused by the proximity.

One device capable of detecting the static magnetic component of a wave is the Superconducting Quantum Interference device, or "SQUID." SQUIDS are highly sensitive, extremely expensive magnetometers. However, SQUIDS only detect the presence of strong waves. A typical vital field generated by an organism has weak vital waves that SQUIDS cannot detect. Further, SQUIDS do not detect the spectral information needed analyze a vital field.

A detection device that is inexpensive, reliable, and capable of detecting vital fields is needed. Therefore, it is an object of the present invention to reliably detect and analyze vital fields. It is a further object that the vital fields be detected with a device that is relatively inexpensive compared to known devices. It is another object of the invention that the device and method of detection reduces unwanted artifacts by not contacting the organism.

SUMMARY OF THE INVENTION

The present device is placed in a vital field such that the vital waves in the vital field are conducted into a detector having an avalanche diode and an avalanche initiator. The avalanche diode is preferably an avalanche photodiode ("APD"). The APD is reverse biased and the bias voltage is supplied by a voltage source. The avalanche initiator impacts the avalanche diode with sufficient energy to generate seed electrons for the electron avalanche process. The energy provided by the avalanche initiator to the avalanche diode may be continuous or pulsed. The avalanche initiator is preferably an optical energy source, and most preferably a silicon vertical cavity surface emitting laser ("VCSEL"), but may be a high-electronvolt generator if the avalanche diode is not a photo-diode. Preferably, the vital waves are conducted into the active region of the APD through a focusing horn to concentrate the energy.

Control circuitry provides a first control signal at a first sampling frequency to the detector. The first control signal is chosen to undersample the vital waves from the vital field, which have very high frequency. The first control signal modulates the gain of the avalanche diode. The avalanche initiator provides sufficient energy to the avalanche diode to create free electrons that start the avalanche process. During the period of increased gain, the vital waves from the vital field cause a detectable interference with the electric field in the active region of the avalanche diode, producing a first mixed signal including a first beat frequency that is the difference between the frequency of the vital waves and a high harmonic of the first sampling frequency.

The first mixed signal is conducted to signal processing circuitry, which filters the signal and applies Fourier transforms. Extraction of the beat frequency from the first mixed signal indicates that the vital waves are present. Then, the control circuitry is adjusted to produce a second control signal and the detection process repeats, producing a second mixed signal with a second beat frequency. The signal processing circuitry uses the first and second beat frequencies to determine the frequency of the vital waves from the vital field. The results of the signal processing are then displayed on a screen. Both the control circuitry and the signal processing circuitry include components that work to limit noise and other artifacts generated during the detection process.

Through continued use of the device, a reference database is developed to associate vital fields with the organisms, organs, organic material, metaphysical changes, or conditions presumed to generate the vital fields.

DETAILED DESCRIPTION OF THE INVENTION

Figure 1:
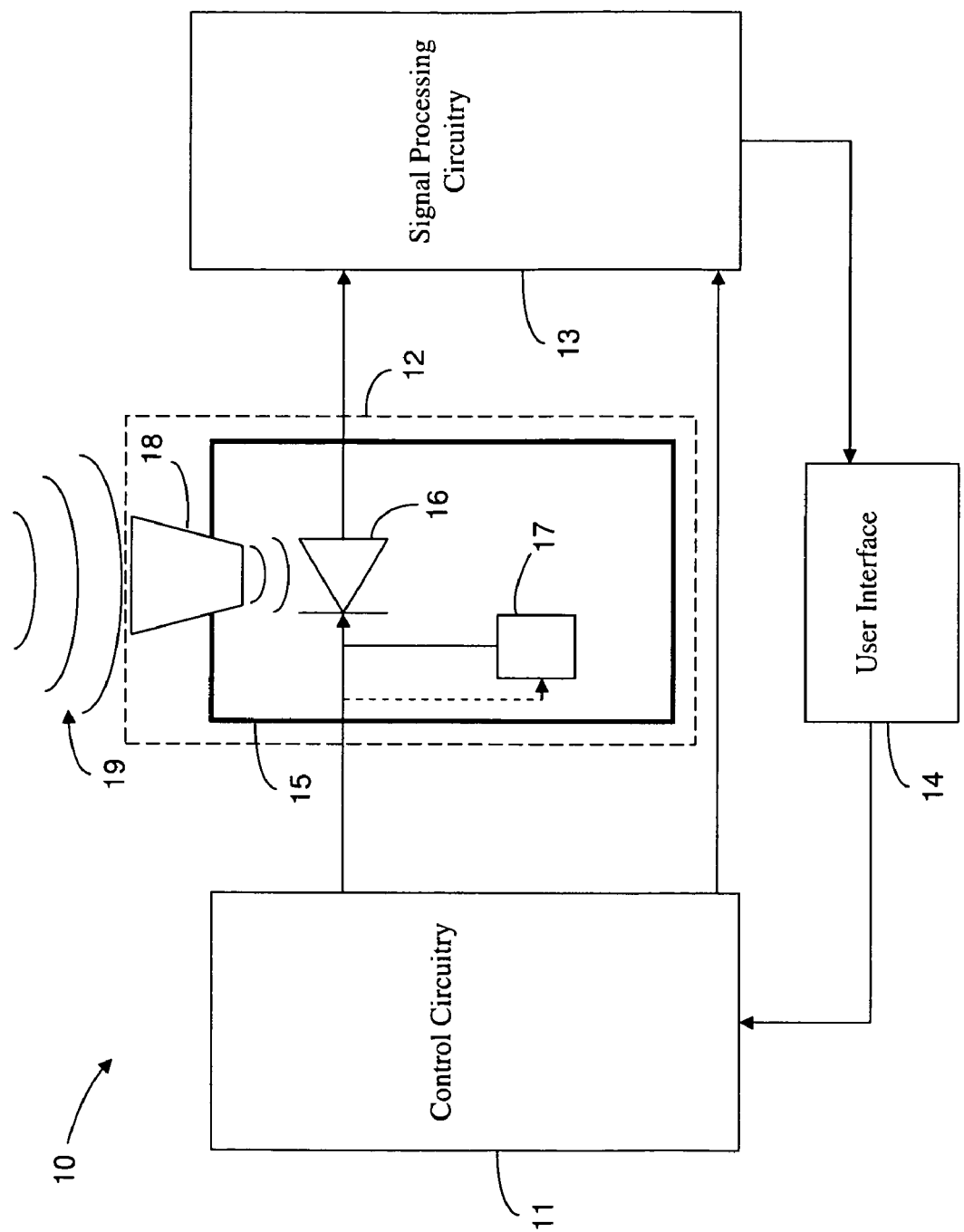
FIG. 1 is a schematic diagram of the present device.

FIG. 1 illustrates the present invention, which is a device 10 for detecting and analyzing vital fields. The device 10 is placed in the path of vital waves 19 that are present in the vital field to be detected. The detection process is initiated through a user interface 14, such as by pressing a button or a designated part of a touch screen that indicates to control circuitry 11 that the process should begin. The control circuitry 11 then generates, as described in detail below, a first control signal having a first sampling frequency, and sends the first control signal to a detector 12. The control circuitry 11 may also send the first control signal to signal processing circuitry 13 for use in a frequency converter as described below.

To achieve the desirably high sensitivity of the device 10, the detector 12 may be substantially enclosed by electromagnetic shielding 15. The shielding 15 protects the internal components of the detector 12 from unwanted interference by light and other electromagnetic waves. The shielding 15 may be a Faraday cage or other shielding structure. If light-sensitive components are not used, the shielding 15 may be a mesh of conducting material, but preferably the shielding 15 fully encloses the detector's 12 internal components, except that a small opening may be left in the shielding to allow the vital waves 19 to pass into the detector 12. In the preferred embodiment, this opening is covered by an opaque dielectric material (not shown) that blocks light but allows the vital waves 19 to pass. The dielectric material may be any electrical insulator, including insulating tape such as vinyl, plastic, or polyester tape. Preferably, the dielectric material is black polyester tape.

The internal components of the detector 12 include an avalanche diode 16 and an avalanche initiator 17 that cooperate to control the parameters of an electron avalanche. The electron avalanche amplifies the signal passing through the avalanche diode 16 by a multiplication factor, known as the gain, which is inversely proportional to the difference between the avalanche diode's 16 breakdown voltage and the voltage applied to the avalanche diode 16. The vital waves 19 entering the device are detectable at a high gain. The device 10 is therefore configured to drive the gain as high as possible. The gain is limited by the intrinsic resistance of the avalanche diode 16 but preferably the peak gain is at least 20,000 and most preferably about 50,000. The avalanche diode 16 may be any avalanche diode that can achieve this gain range and that has device geometry that allows the vital waves 19 to propagate substantially parallel to the electron avalanche, including a standard avalanche diode, a modified Zener diode, or an APD. The diode may use any suitable semiconducting material, including silicon, germanium, and InGaAs, and may be doped to increase the gain range. The diode may alternatively propagate the signal through an air avalanche, but a semiconducting material is preferable because it will have a much lower impedance than air. Preferably, the avalanche diode 16 is a doped silicon APD. The avalanche diode 16 is reverse biased and a constant voltage is applied to the cathode of the avalanche diode 16 to keep the avalanche diode 16 biased in its linear region. Then, the avalanche diode 16 is modulated to its peak gain as described below.

The avalanche initiator 17 emits energy that impacts the semiconducting material of the avalanche diode 16, causing impact ionization and creating seed electrons for the electron avalanche. The appropriate avalanche initiator 17 will depend on the type of avalanche diode 16 used. In the preferred embodiment, the avalanche initiator 17 is an optoelectronic device with low residual intensity noise and sufficient energy to cause impact ionization in the preferred APD. Suitable devices include lasers such as a VCSEL or fiber laser, and light-emitting diodes such as a resonant cavity light-emitting diode ("RCLED"). The avalanche initiator 17 is most preferably a silicon VCSEL. Alternatively, the electron avalanche may be initiated by voltage alone, such as in a standard avalanche diode, and the avalanche initiator 17 may be a generator functioning as a device electrode and capable of applying enough electronvolts to the avalanche diode 16 to prompt impact ionization. Such an avalanche diode 16 may be doped to allow electron avalanche initiation by voltage alone.

The first control signal is directed to the avalanche diode 16, where it causes the application of a low voltage to the cathode as described below. This low voltage brings the total voltage at the cathode up to within, preferably, several millivolts of the breakdown voltage of the avalanche diode 16. The applied voltage significantly raises the operating gain of the avalanche diode 16 as it approaches the breakdown voltage of the avalanche diode 16. The period of high operating gain is referred to as the high gain period. The low voltage is preferably modulated such that it varies from 0 to between 5 and 10 volts on a sine wave having the first sampling frequency. In the preferred embodiment, the high gain period lasts for between 20 and 50 picoseconds, during which the operating gain is increased from a factor of around 70 to a peak factor of more than 25,000. In the alternate embodiment described below, where a logic level pulse of low voltage is applied to the avalanche diode 16, the high gain period lasts for as much as 10 nanoseconds, and typically between five and 10 nanoseconds.

In the preferred embodiment, described in detail below and in FIG. 2, the avalanche initiator 17 constantly emits energy, most of which impacts the avalanche diode 16. The amount of energy provided to the avalanche diode 16 is adjustable in order to generate approximately a desired number of seed electrons for the electron avalanche. Preferably, a low average number of seed electrons are generated, and most preferably the impact ionization produces an average of five seed electrons during the high-gain period of the avalanche diode 16.

In an alternate embodiment, described in detail below and in FIG. 3, the first control signal is synchronized to provide a current pulse to the avalanche initiator 17 during the high-gain period of the avalanche diode 16. The current pulse causes the avalanche initiator 17 to pulse at the first sampling frequency. Each pulse of the avalanche initiator 17 causes an electron avalanche to propagate through the active region of the avalanche diode 16.

In either described embodiment, the avalanche propagates so quickly, typically within about 100 picoseconds, that the first sampling frequency is retained in the resulting amplified signal that is emitted from the anode of the avalanche diode 16. The resulting signal is called the first mixed signal, as described below.

The vital waves 19 pass into the detector 12 and are incident on the avalanche diode 16. Preferably, a focusing horn 18 is used to concentrate the vital waves 19 into the active region of the avalanche diode 16 where the electron avalanche process takes place. The focusing horn 18 is made of a conductive material, preferably metal, that will reflect the vital waves 19 due to their static electric component. Suitable metals include brass, copper, and aluminum, but most preferably the focusing horn 18 is brass. The focusing horn 18 is soldered to the shielding 15 to prevent light leaks, and the dielectric material is used to cover the end of the focusing horn 18 inside the detector 12.

An electron avalanche requires the presence of a strong electric field in the active region of the avalanche diode 16. This field is static, assuming no interference and a constant applied voltage, and it has a known strength that is dependent on the intrinsic breakdown voltage of the avalanche diode 16 used. However, the incident vital waves 19 also have a static electric component, which interferes with the electric field in the active region and may advance or retard the avalanche process. In the case where the vital waves 19 have extremely high frequencies, of at least 30 gigahertz and further into the terahertz range, undersampling may be used to determine the frequency. The signal propagated through the avalanche diode 16 has sufficient harmonic content that heterodyning occurs between the vital waves 19 and a high harmonic of the first sampling frequency. As a result, the first mixed signal, carried out of the avalanche diode 16 by the amplified current, contains a first beat frequency that is the difference between the frequency of the vital waves 19 and a high harmonic of the first sampling frequency.

The first mixed signal is then processed by signal processing circuitry 13. As described below, the first mixed signal undergoes filtration, optional frequency conversion, and Fourier transformation to extract the desired frequency data. During or after this processing, the control circuitry generates a second control signal having a second sampling frequency and sends it to the detector 12, resulting in a second mixed signal having a second beat frequency. The second mixed signal is also processed by signal processing circuitry 13. The second beat frequency is subtracted from the first beat frequency to obtain the beat frequency shift.

The harmonic with which the vital waves 19 were heterodyned is determined by dividing the sampling frequency shift by the beat frequency shift. The harmonic number of the first sampling frequency then allows calculation of the observed frequency imparted by the vital waves 19. The detection process may be repeated with additional sampling frequencies to reduce uncertainties if multiple vital wave 19 frequencies are present.

The spectral data of the detection process may be formatted and displayed on a screen in the user interface 14. Further, the spectral data may be compared to records in a reference database to determine if it matches information gathered on known vital fields. In this manner, if it has been determined that certain data previously gathered by the device 10 correlates to, for example, the presence of a blood disease or its precursors, the results of the detection process may be compared to the previously collected data to determine if the scanned person has the same disease or its precursors. Reference databases may be generated for specific plants and animals, and may be used to detect vital fields associated with bodily states and conditions, the presence or absence of diseases, and aspects of other body energies such as chakra or qi.

Figure 2:
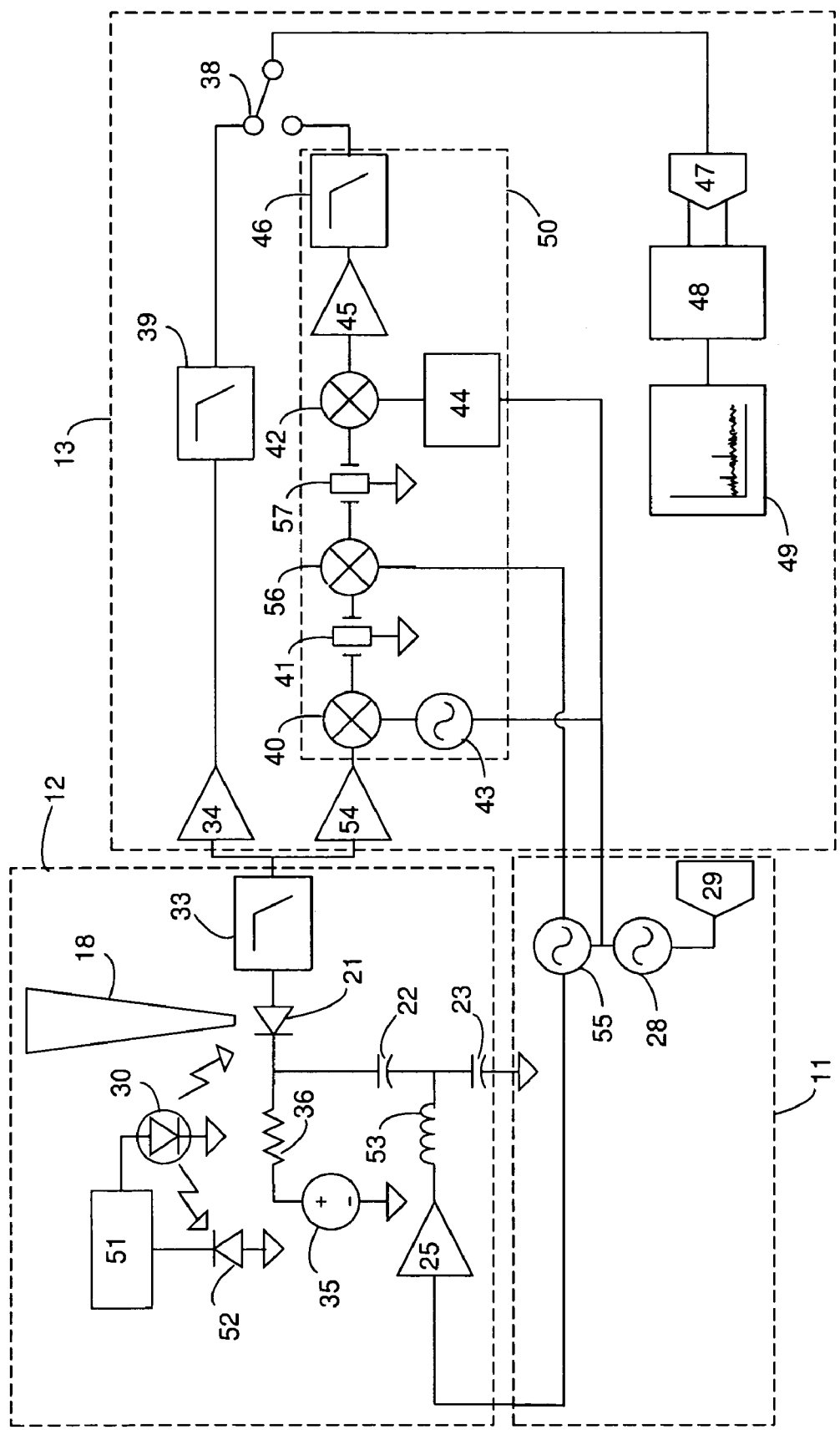
FIG. 2 is a circuit diagram of the preferred embodiment of the present device.

Referring to FIG. 2, the preferred embodiment of the device 10 utilizes a silicon APD 21. These devices are capable of a very high operating gain, which corresponds to desirably high sensitivity in detecting the weak vital waves in a vital field. However, APDs are also susceptible to significant noise due to their sensitivity. Therefore, the preferred embodiment of the present device endeavors to minimize noise in the circuit using components that filter unwanted signals and maintain low impedance on sensitive elements.

When the detection process is initiated, a master clock oscillator 28 supplies the master clock frequency to a signal source 55, which produces the first control signal at the first sampling frequency. The master clock oscillator 28 is preferably a voltage controlled crystal oscillator, allowing the frequency to be controlled by a digital-to-analog converter 29. Alternatively, the master clock oscillator 28 may be a frequency synthesizer. The signal source 55 is a frequency synthesizer. The signal source 55 sends the first control signal into the detector 12.

Within the detector 12, a pulse buffer 25 provides a low impedance drive for the APD 21 bias modulation. The pulse buffer 25 is a transistor amplifier, either discrete or part of an integrated circuit, and is preferably a GaAs monolithic microwave integrated circuit ("MMIC"). Alternatively, a MMIC using a different semiconducting material, or a CMOS inverter, may be used. A pulse inductor 53 performs impedance matching to maximize power transfer to the APD 21. The pulse capacitor 22 and high-stop capacitor 23 present low impedance on the cathode of the APD 21. The pulse capacitor 22 also couples a periodic low voltage onto the APD 21 bias. In a typical embodiment, the low voltage modulates in a sine wave having the first sampling frequency and a maximum amplitude of between five and 10 volts, which will sum with a constant high voltage bias to raise the applied voltage to just below the breakdown voltage of the APD 21. During this modulation, the avalanche gain will peak at over 25,000 for about 35 picoseconds. The voltage source 35 supplies the high voltage bias to the APD 21. The voltage level is controlled by an external computer processor. The voltage is adjusted to give a fixed current through the bias resistor 36. The bias resistor 36 also forms a low pass noise filter with the pulse capacitor 22. The pulse capacitor 22 coupling, low pass filtration, and low impedance together reduce noise contributed by the APD 21 dark current or light leakage in the vicinity of the APD 21. Modulation of the APD 21 gain also eliminates any potential problems with sensitivity reduction due to the APD 21 gain-bandwidth product, because ejected electrons are more quickly replenished in the active region during periods of low gain. Noise from the dark current, caused by impurities in the APD 21, is further reduced by keeping the active region of the APD 21 very small.

The VCSEL 30 has low noise but may be susceptible to temperature or manufacture variation that affects the consistency of emitted light. Therefore, an automatic level control circuit ("ALC") 51 provides an adjustable current to the VCSEL 30. The current from the ALC 51 causes the VCSEL 30 to emit a substantially constant amount of light, most of which impacts the APD 21. Some of the light hits a monitor diode 52, preferably a PIN diode, that detects the amount of light being emitted and signals the ALC 51 to adjust the current if the amount is outside the range needed to generate the desired average number of seed electrons by impact ionization of the semiconducting material in the APD 21. In an alternate embodiment using an RCLED as the avalanche initiator 17, an ALC 51 and monitor diode 52 may not be needed due to the RCLED being much less sensitive to temperature than a VCSEL.

The fewer the number of seed electrons, the higher the possible avalanche gain and hence, the sensitivity. However, with a sufficiently small number of seed electrons, the quantized nature of electron charge introduces quantization noise which limits the sensitivity. Preferably, at least five seed electrons are generated by an optical pulse, and most preferably exactly five. The signal is multiplied exponentially due to the nature of the electron avalanche process, and this effect is magnified by modulating the high-gain period of the APD 21. Modulation at the first sample frequency creates harmonics that are beyond the harmonic content of the first control signal.

Because the APD 21 is biased in the linear region, the avalanche gain is limited by the intrinsic impedance of the APD 21, including any parasitic reactance associated with the APD 21. The APD 21 must see a short circuit at high frequencies, particularly between 2 and 3 gigahertz, to minimize this intrinsic impedance and also to eliminate frequencies that are contributed to the mixed signal by the APD 21 geometry. The short circuit is provided by a short-circuit lowpass filter 33, which has a cutoff frequency of half the first sampling frequency. The short-circuit lowpass filter 33 therefore suppresses the first sampling frequency, preventing overload of the signal processing circuitry. In the preferred embodiment, the short-circuit lowpass filter 33 is a lumped element filter. The baseband DC amplifier 34 and baseband AC amplifier 54 both present a suitable terminating impedance for the short-circuit lowpass filter 33 and set the baseband noise floor after the APD 21. The baseband DC amplifier 34 is DC coupled and is used if the first mixed signal has a low enough frequency to be passed through an analog-to-digital converter ("ADC") 47. The baseband AC amplifier 54 is AC coupled and filters out the DC portion of the first mixed signal if a frequency conversion is needed.

The first mixed signal, now a baseband signal, may be routed through a frequency converter 50. This is not a necessary step, but it can provide a more practical realization by allowing a sampling frequency that is much higher than the ADC 47 sampling rate. Because most signals of interest are undersampled, doubling the sampling frequency will produce about a 3 decibel improvement in signal to noise ratio. Within the frequency converter 50, the first intermediate frequency mixer 40 provides frequency conversion to a first intermediate frequency ("IF") by mixing the first mixed signal with a signal generated by the first local oscillator 43. The first local oscillator 43 is preferably a frequency synthesizer that is in phase lock with the master clock oscillator 28. Preferably, the IF is 916.36 megahertz to allow the use of an inexpensive inline surface acoustic wave ("SAW") filter for the first IF filter 41. The first IF filter 41 then provides image rejection in the down-converted signal to improve the performance of a second IF mixer 56. The second IF mixer 56 converts the first mixed signal to a frequency of 10.7 megahertz to allow the use of a ceramic filter as a second IF filter 57, which provides high quality noise filtering of the signal. The sampling mixer 42 mixes the IF with a signal from a second local oscillator 44 to convert the first mixed signal down to a suitable range for the ADC 47 sampling rate. The second local oscillator 44 is preferably a frequency divider that takes the master clock signal as an input. The switch 38 is used to bypass the frequency converter 50. Anti-alias lowpass filter 39 provides anti-aliasing filtering of the baseband first mixed signal when the frequency converter 50 is bypassed.

With a master clock of 44 megahertz, the second local oscillator 44 signal is 11 megahertz, the first sample frequency is 905.66 megahertz, and the baseband first mixed signal ranges from 0 to 452.83 megahertz. These frequencies are chosen to allow the use of low cost ceramic and SAW filters. Additionally, a sampling frequency at or near 1 gigahertz allows the use of smaller Fourier transforms during signal processing. The smaller transforms account for both random variation in detected frequencies and frequency drift in the signal source 55. The frequency converter 50 loss is corrected by a converter amplifier 45. Any out of band noise from the converter amplifier 45 is removed by a converter lowpass filter 46.

The baseband signal is digitized by ADC 47. A Fourier transform computer 48 computes a large fast Fourier transform ("FFT") to detect the desired signals, such as the first beat frequency, within the baseband signal. After the detection process is run a second time to acquire a second beat frequency, the computer 48 calculates the input frequency. The FFT results are processed and displayed on the screen 49.

Figure 3:
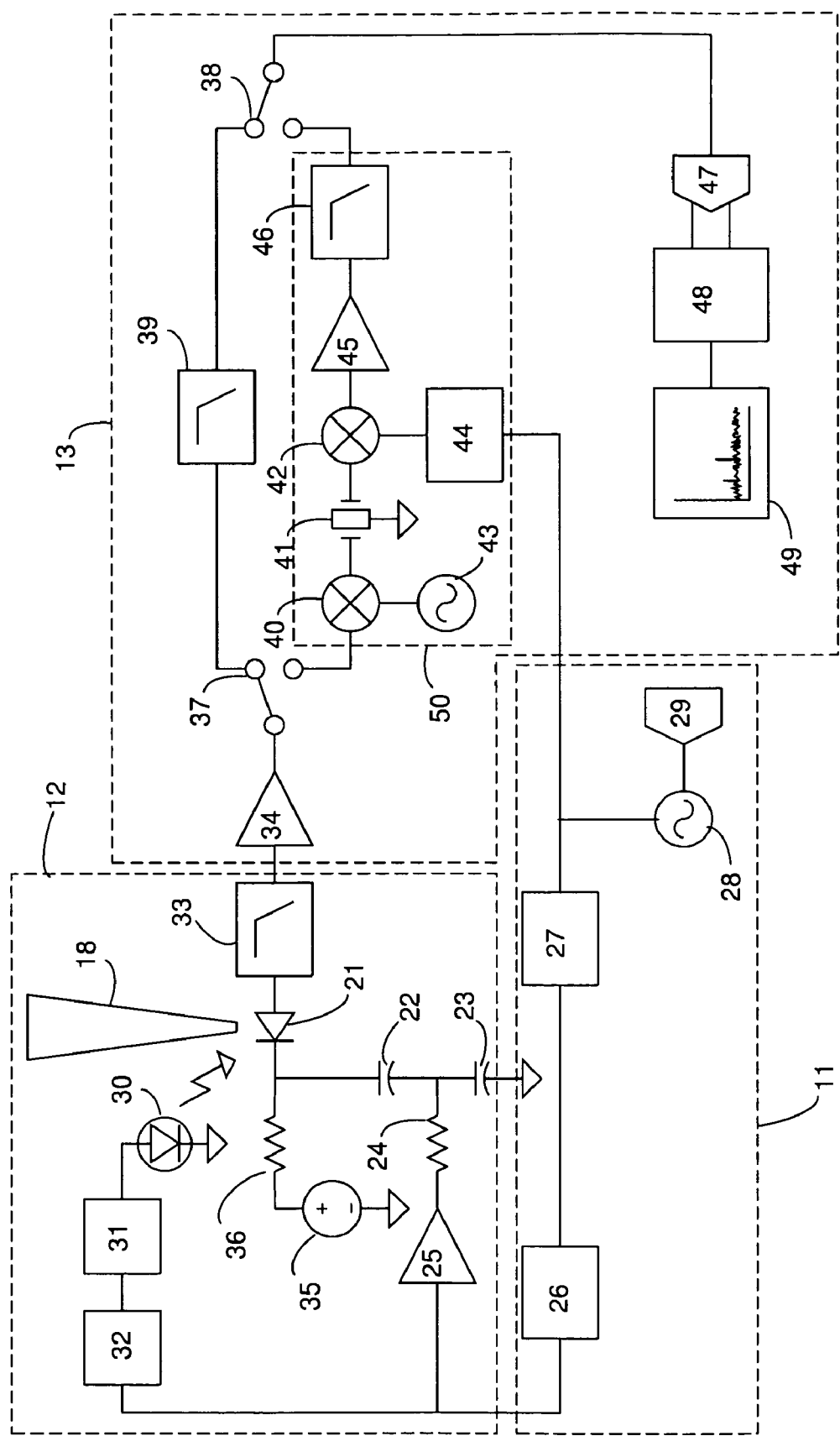
FIG. 3 is a circuit diagram of an alternate embodiment of the present device.

Referring to FIG. 3, an alternate embodiment of the device 10 utilizes a silicon APD 21 and a silicon VCSEL 30. When the detection process is initiated, the master clock oscillator 28 supplies the master clock frequency to a clock frequency divider 27, which produces the first sampling frequency. The clock frequency divider 27 supplies the first sampling frequency to an asynchronous state machine ("ASM") 26 that generates a narrow pulse on one edge of the incoming waveform. The ASM 26 is preferably a gate and inverter, generating a first control signal having the first sampling frequency and a pulse length of several nanoseconds. The first control signal is sent into the detector 12.

Within the detector 12, the pulse buffer 25 provides a low impedance drive for the APD 21 bias pulsing. A pulse resistor 24 forms a low pass filter with high-stop capacitor 23 to limit the rate of APD 21 bias change. The pulse capacitor 22 and high-stop capacitor 23 present low impedance on the cathode of the APD 21. The pulse capacitor 22 also couples a periodic low voltage onto the APD 21 bias. In a typical embodiment, the logic level pulse has a maximum voltage of about 2V, which will raise the biased voltage to just below the breakdown voltage of the APD 21 and raise the avalanche gain from 70 to about 20,000 for several nanoseconds. The voltage source 35 supplies the high voltage bias to the APD 21. The voltage level is controlled by an external computer processor. The voltage is adjusted to give a fixed current through the bias resistor 36. The bias resistor 36 also forms a low pass noise filter with the pulse capacitor 22.

The time delay circuit 32 produces a time delay to align an optical pulse with the APD 21 high gain period. The time delay circuit 32 is a logic device or a resistor-capacitor circuit chosen to cause the desired delay while retaining the incoming signal frequency. A pulse generator 31, preferably a regenerative switch, provides a current pulse to the VCSEL 30 on the rising edge of the first control signal. Alternatively, the pulse generator 31 may be a step recovery diode. The pulse generator 31 produces a pulse that is sufficient to cause the VCSEL 30 to emit a very short pulse of light. The duration of the light pulse is made as short as possible while emitting sufficient energy to generate approximately the preferred number of seed electrons in the APD 21, as described below. For a VCSEL with 3 gigahertz bandwidth, the pulse is preferably in the range of 50-100 picoseconds. The pulse may be even shorter if a fiber laser is used.

The short circuit of high APD 21 frequencies is provided by short-circuit lowpass filter 33, which has a cutoff frequency of half the first sampling frequency. In the present embodiment, short-circuit lowpass filter 33 is a lumped element filter. The baseband amplifier 34 presents a suitable terminating impedance for the short-circuit lowpass filter 33, and sets the baseband noise floor after the APD 21.

The first mixed signal, now a baseband signal, may be routed through a frequency converter 50. Within the frequency converter 50, intermediate frequency mixer 40 provides frequency conversion to the IF by mixing the first mixed signal with a signal generated by the first local oscillator 43. In the present embodiment, the first local oscillator 43 is a direct digital frequency synthesizer that tunes from 11.0 to 17.8 megahertz. Preferably, the IF is 10.7 megahertz to allow the use of inexpensive ceramic filters for the first IF filter 41. In the present embodiment, the first IF filter 41 is a ceramic filter that provides high quality noise filtering of the downconverted signal. The sampling mixer 42 mixes the IF with a signal from a second local oscillator 44 to convert the first mixed signal down to a suitable range for the ADC 47 sampling rate. The second local oscillator 44 is preferably a frequency divider that takes the master clock signal as an input. Switches 37 and 38 are used to bypass the frequency converter 50 at low frequencies if desired. Anti-alias lowpass filter 39 provides anti-aliasing filtering of the baseband first mixed signal when the frequency converter 50 is bypassed.

With a master clock of 44 megahertz, the second local oscillator 44 signal is 11 megahertz, the first sample frequency is 14.66 megahertz, and the baseband first mixed signal ranges from 0 to 7.33 megahertz. These frequencies are chosen to allow the use of low cost ceramic filters, and the use of low cost CMOS analog switches for frequency mixing. The frequency converter 50 loss is corrected by a converter amplifier 45. Any out of band noise from the converter amplifier 45 is removed by a converter lowpass filter 46.

The baseband signal is digitized by ADC 47. A Fourier transform computer 48 computes a large fast Fourier transform ("FFT") to detect the desired signals, such as the first beat frequency, within the baseband signal. After the detection process is run a second time to acquire a second beat frequency, the computer 48 calculates the input frequency. The FFT results are processed and displayed on the screen 49.

While there has been illustrated and described what is at present considered to be the preferred embodiment of the present invention, it will be understood by those skilled in the art that various changes and modifications may be made and equivalents may be substituted for elements thereof without departing from the true scope of the invention. Therefore, it is intended that this invention not be limited to the particular embodiment disclosed, but that the invention will include all embodiments falling within the scope of the appended claims.

We claim:

1. A device for detecting and analyzing vital fields, the device comprising:
   a) control circuitry configured to generate a first control signal at a first sampling frequency and a second control signal at a second sampling frequency different from the first sampling frequency;
   b) a detector in electrical communication with the control circuitry, the detector comprising:
      i. an avalanche diode having an active region on which vital waves from the vital field are incident;
      ii. an avalanche initiator configured to provide energy to the avalanche diode, the energy generating seed electrons for electron avalanches;
      iii. a capacitor coupled to the avalanche diode's cathode and configured to periodically apply a low voltage to the cathode; and
      iv. electromagnetic shielding substantially enclosing the avalanche diode and the avalanche initiator such that the electromagnetic shielding prevents unwanted electromagnetic interference with the electron avalanches but allows the vital waves to pass; and
   c) signal processing circuitry in electrical communication with the detector;
   wherein:
   a) the control circuitry sends the first control signal to the detector;
   b) the first control signal causes the capacitor to modulate high gain operation of the avalanche diode at the first sampling frequency by applying the low voltage to the cathode at the first sampling frequency;
   c) an input frequency from the vital waves mixes with a harmonic of the first sampling frequency in the active region of the avalanche diode during high gain operation of the avalanche diode, generating a first mixed signal having a first beat frequency;
   d) the avalanche diode sends the first mixed signal to the signal processing circuitry;
   e) the control circuitry sends the second control signal to the detector;
   f) the second control signal causes the capacitor to modulate high gain operation of the avalanche diode at the second sampling frequency by applying the low voltage to the cathode at the second sampling frequency;
   g) the input frequency from the vital waves mixes with a harmonic of the second sampling frequency in the active region of the avalanche diode during high gain operation of the avalanche diode, generating a second mixed signal having a second beat frequency;
   h) the avalanche diode sends the second mixed signal to the signal processing circuitry; and
   i) the signal processing circuitry determines the input frequency from the vital waves using the first and second beat frequencies.

2. The device of claim 1 wherein the avalanche initiator constantly provides energy to the avalanche diode, and wherein the detector further comprises a level control circuit configured to provide an adjustable current to the avalanche initiator.

3. The device of claim 2 wherein the detector further comprises a monitoring diode configured to monitor the amount of energy output by the avalanche initiator and to signal the level control circuit if the amount of energy is out of a desired range.

4. The device of claim 1 wherein the detector further comprises a focusing horn connected to the electromagnetic shielding and positioned to concentrate the vital waves into the active region of the avalanche diode.

5. The device of claim 1 wherein the detector further comprises a short-circuit lowpass filter configured to make the first and second mixed signals baseband signals.

6. The device of claim 1 wherein the signal processing circuitry comprises a Fourier transform computer configured to extract frequency data from the first and second mixed signals.

7. The device of claim 6 wherein the signal processing circuitry further comprises a frequency converter configured to simplify the extraction of frequency data by the Fourier transform computer.

8. The device of claim 6 wherein the signal processing circuitry further comprises a screen for displaying frequency data extracted by the Fourier transform computer.

9. A device for detecting and analyzing vital fields, the device comprising:
- a) control circuitry configured to generate a control signal at a desired sampling frequency;
- b) a detector in electrical communication with the control circuitry, the detector comprising:
  - i. a silicon avalanche photodiode having an active region on which vital waves from the vital field are incident;
  - ii. a voltage source configured to supply a substantially constant voltage to the avalanche photodiode's cathode;
  - iii. a pulse capacitor configured to apply a low voltage to the avalanche photodiode's cathode at the sampling frequency, such that the sum of the substantially constant voltage and the low voltage is slightly below the avalanche photodiode's breakdown voltage and places the avalanche photodiode into a high gain period;
  - iv. a silicon vertical cavity surface emission laser ("VCSEL") configured to send substantially constant laser energy into the avalanche photodiode, wherein the laser energy generates a low average number of seed electrons for an electron avalanche;
  - v. an automatic level control circuit configured to supply the VCSEL with an adjustable current;
  - vi. a monitoring diode that monitors the amount of laser energy output by the VCSEL and signals the automatic level control circuit if the amount is outside a desired range;
  - vii. a Faraday cage substantially enclosing at least the avalanche photodiode, the VCSEL, and the monitoring diode;
  - viii. a brass focusing horn connected to the Faraday cage and having an opening inside the Faraday cage, the brass focusing horn positioned to concentrate the vital waves into the active region of the avalanche photodiode so that an input frequency from the vital waves mixes with a harmonic of the sampling frequency in the active region of the avalanche diode during the high gain period, generating a mixed signal having a beat frequency;
  - ix. an opaque dielectric material covering the focusing horn's opening inside the Faraday cage; and
  - x. a short-circuit lowpass filter configured to receive the mixed signal from the avalanche photodiode and short-circuit frequencies in the mixed signal that are at or higher than half the sampling frequency; and
- c) signal processing circuitry in electrical communication with the detector, the signal processing circuitry comprising:
  - i. a baseband amplifier that receives the mixed signal from the short-circuit lowpass filter and amplifies the mixed signal;
  - ii. a baseband lowpass filter that receives the mixed signal from the baseband amplifier and filters noise caused by amplification;
  - iii. an analog-to-digital converter that receives the mixed signal from the baseband lowpass filter and converts it from analog to digital; and
  - iv. a Fourier transform computer that receives the mixed signal from the analog-to-digital converter, extracts frequency data including the beat frequency from the mixed signal, and processes the frequency data to obtain spectral data about the vital waves.

10. A method of detecting and analyzing a vital field, the method comprising:
- a) generating a first control signal having a first sampling frequency and a second control signal having a second sampling frequency;
- b) positioning an avalanche diode in the vital field so that vital waves from the vital field are incident upon the avalanche diode's active region;
- c) using the first control signal to generate a first mixed signal having a first beat frequency by:
  - i. sending the first control signal to the avalanche diode so that the gain of the avalanche diode is modulated at the first sampling frequency; and
  - ii. initiating electron avalanches in the avalanche diode using energy provided by an avalanche initiator so that the modulated gain generates a harmonic of the first sampling frequency that mixes with an input frequency of the vital waves to cause the avalanche diode to output the first mixed signal;
- d) using the second control signal to generate a second mixed signal having a second beat frequency by:
  - i. sending the second control signal to the avalanche diode so that the gain of the avalance diode is modulated at the second sampling frequency; and
  - ii. initiating electron avalanches in the avalanche diode using energy provided by an avalanche initiator so that the modulated gain generates a harmonic of the second sampling frequency that mixes with the input frequency of the vital waves to cause the avalanche diode to output the second mixed signal; and
- e) determining the input frequency of the vital waves by:
  - i. finding the beat frequency shift between the first beat frequency and the second beat frequency;
  - ii. using the beat frequency shift to determine the frequency of the harmonic of the first sampling frequency that mixed with the input frequency; and
  - iii. adding the first beat frequency to the frequency of the harmonic of the first sampling frequency.

* * * * *